US008461186B2

(12) United States Patent
Merizzi

(10) Patent No.: US 8,461,186 B2
(45) Date of Patent: Jun. 11, 2013

(54) USE OF N-PIPERIDINE DERIVATIVES FOR THE TREATMENT OF NEURODEGENERATIVE PATHOLOGIES

(75) Inventor: Gianfranco Merizzi, Turin (IT)

(73) Assignee: Medestea Research & Production S.p.A., Colleretto Giacosa (Torino) (IT)

( * ) Notice: Subject to any disclaimer, the term of this patent is extended or adjusted under 35 U.S.C. 154(b) by 1142 days.

(21) Appl. No.: 10/589,469

(22) PCT Filed: Feb. 22, 2005

(86) PCT No.: PCT/EP2005/001818
§ 371 (c)(1),
(2), (4) Date: Aug. 14, 2006

(87) PCT Pub. No.: WO2005/084677
PCT Pub. Date: Sep. 15, 2005

(65) Prior Publication Data
US 2007/0191427 A1    Aug. 16, 2007

(30) Foreign Application Priority Data

Mar. 1, 2004 (IT) .............................. TO2004A0124

(51) Int. Cl.
*A61K 31/44* (2006.01)
(52) U.S. Cl.
USPC ........................................................ 514/335
(58) Field of Classification Search
USPC ........................................................ 514/335
See application file for complete search history.

(56) References Cited

U.S. PATENT DOCUMENTS

| 4,691,015 | A | | 9/1987 | Behrens et al. | |
| 4,883,666 | A | | 11/1989 | Sabel et al. | |
| 5,036,097 | A | * | 7/1991 | Floyd et al. | 514/400 |
| 5,637,578 | A | | 6/1997 | Riley et al. | |
| 5,696,109 | A | | 12/1997 | Malfroy-Carmine et al. | |
| 5,874,421 | A | | 2/1999 | Riley et al. | |
| 5,981,548 | A | | 11/1999 | Paolini et al. | |
| 6,117,454 | A | | 9/2000 | Kreuter et al. | |
| 6,420,429 | B1 | * | 7/2002 | Atlas et al. | 514/625 |
| 2005/0065182 | A1 | | 3/2005 | Papazoglou | |

FOREIGN PATENT DOCUMENTS

| EP | 1 132 085 | 9/2001 |
| WO | WO 02/28390 | 4/2002 |
| WO | WO 02/058686 | 8/2002 |
| WO | WO 2005/032479 | 4/2005 |

OTHER PUBLICATIONS

Miller DB and O'Callaghan JP, "Do early-life insults contribute to the late-life development of Parkinson and Alzheimer diseases?" Metabolism, Oct. 2008, 57(Suppl 2), S44-S49.*
Bloom FE Chapter 12 Neurotransmissions and the Central Nervous System, "Goodman & Gilman's The Pharmacological Basis of Therapeutics, 10th ed." Hardman JG, Limbird LE, and Gilman AG, Eds., McGraw-Hill, 2001, 293-320 (pp. 293 and 297 provided).*
Wilkinson GR, Chapter 1 Pharmacokinetics—The Dynamics of Drug Absorption, Distribution, and Elimination, "Goodman & Gilman's The Pharmacological Basis of Therapeutics, 10th ed." Hardman JG, Limbird LE, and Gilman AG, Eds., McGraw-Hill, 2001, 3-30 (pp. 3 and 10 provided).*
Guan Zhi-Zhong et al., "Loss of nicotinic receptors induced by beta-amyloid peptides in PC12 cells: Possible mechanism involving lipid peroxidation", Journal of Neuroscience Research, vol. 71, No. 3, Feb. 1, 2003, pp. 391-406, XP009050302.
Sotonyi Peter et al, "Comparative study of cardiotoxic effect of Tinuvin 770: a light stabilizer of medical plastics in rat model", Toxological Sciencies: An Official Journal of the Society of Toxicology, Feb. 2004, vol. 77, No. 2, Feb. 2004, pp. 368-374, XP 002334830.
Database PUBMED Online, Department of Health and Human Services, Aug. 2002, Levin ED, Rezvani AH, "Nicotinic Treatment for Cognitive Disorders", XP002334833, Database accession No. 12769614 abstract & Current Drug Targets—CNS and Neurological Disorders, vol. 1, No. 4, Aug. 2002, pp. 423-431, ISSN: 1568-007X.
Hernandez CM et al., "Regional and sub-type specific upregulation of cholinergic receptors with nicotine, mecamylamine and cotinine", Society for Neuroscience Abstracts, vol. 27, No. 2, 2001, p. 2133, XP001206875 & 31$^{st}$ Annual Meeting of the Society for Neuroscience; San Diego, CA, USA; Nov. 10-15, 2001 ISSN: 0190-5295 abstract.

(Continued)

*Primary Examiner* — Paul Zarek
(74) *Attorney, Agent, or Firm* — Roylance, Abrams, Berdo & Goodman, L.L.P.

(57) ABSTRACT

The present invention relates to chemical compounds, to pharmaceutical and veterinary compositions, and to the use of such compositions for the treatment or prevention of neurodegenerative pathologies and syndromes such as Parkinson's disease, Alzheimer's disease, lesions due to ischaemia and reperfusion, traumatic brain lesions, neuropathy due to HIV, Down's syndrome, diabetic polyneuropathy, muscular dystrophy, multiple sclerosis, Huntington's disease, prion disease, late dyskinesia, tauopathy and demyelinating pathologies, and other life-threatening pathologies such as cardiac/renal/pulmonary/hepatic/intestinal ischaemia-reperfusion, hypertension, diabetes, cancer, shock, toxicity due to drugs and radiation (radiotherapy and radiation protection), inflammatory conditions, atherosclerosis, aging, hyperlipidaemia, hypercholesterolaemia, epilepsy, and rheumatoid arthritis, all of which are known to be associated with an excess production of reactive free radicals. More particularly, the present invention relates to compositions containing antioxidant cyclic (bis)-hydroxylamines derived from N-piperidine as pharmaceutical compositions for the prevention and treatment of pathologies in man and in animals.

11 Claims, 2 Drawing Sheets

OTHER PUBLICATIONS

Francis Michael M. et al., "Sensitivity to voltage-independent inhibition determined by pore-lining region of the acetylcholine receptor", Biophysical Journal, vol. 74, No. 5, May 1998, pp. 2306-2317, XP002334831, ISSN: 0006-3495 abstract p. 2307, col. 2, paras. 3-5, p. 2312, col. 2, last para.—p. 2313, col. 2, para. 2, p. 2316, col. 1, para. 2.

Graham John H et al., "Functional central nicotinic acetylcholine receptor antagonism by systemic administraiton of Tinuvin 770 (BTMPS)", Current Alzheimer Research, Apr. 2005, vol. 2, No. 2, Apr. 2005, pp. 141-147, XP001206874.

* cited by examiner

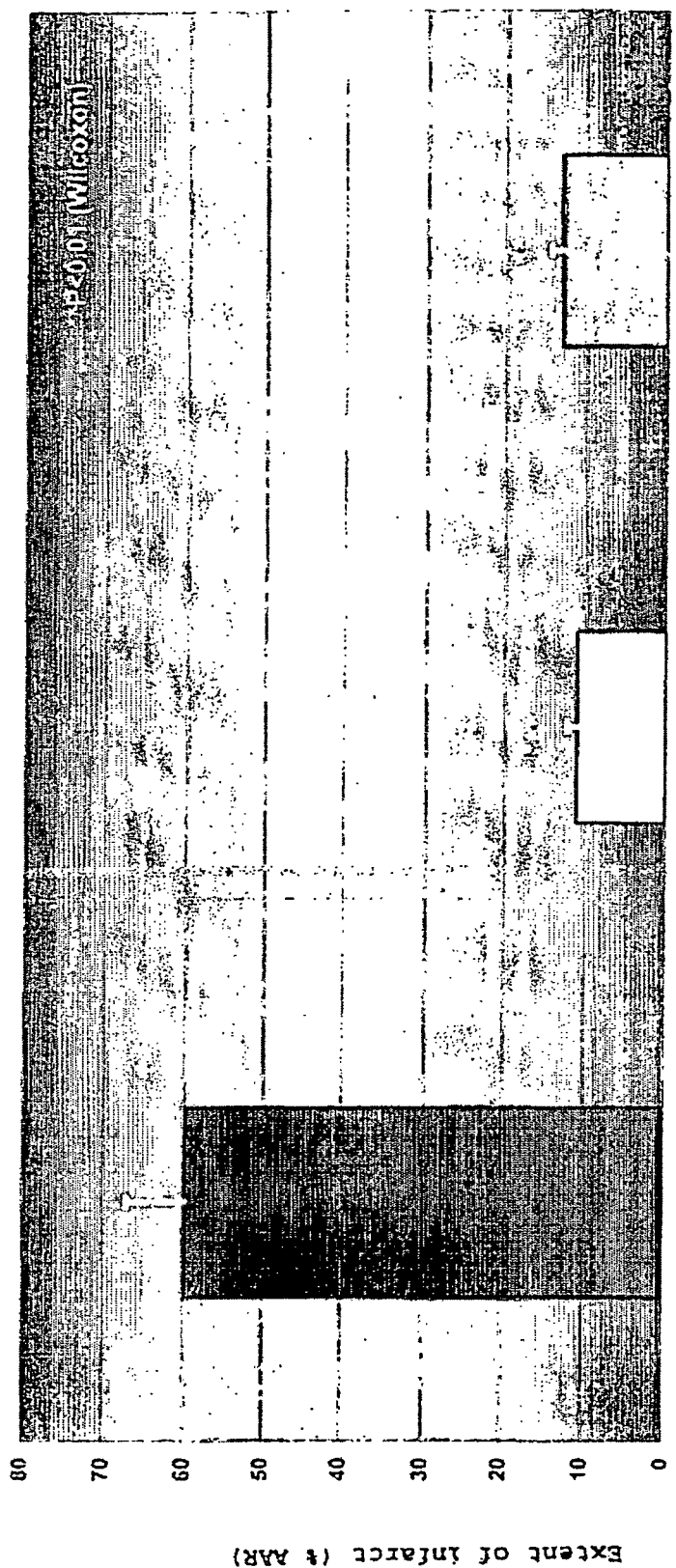

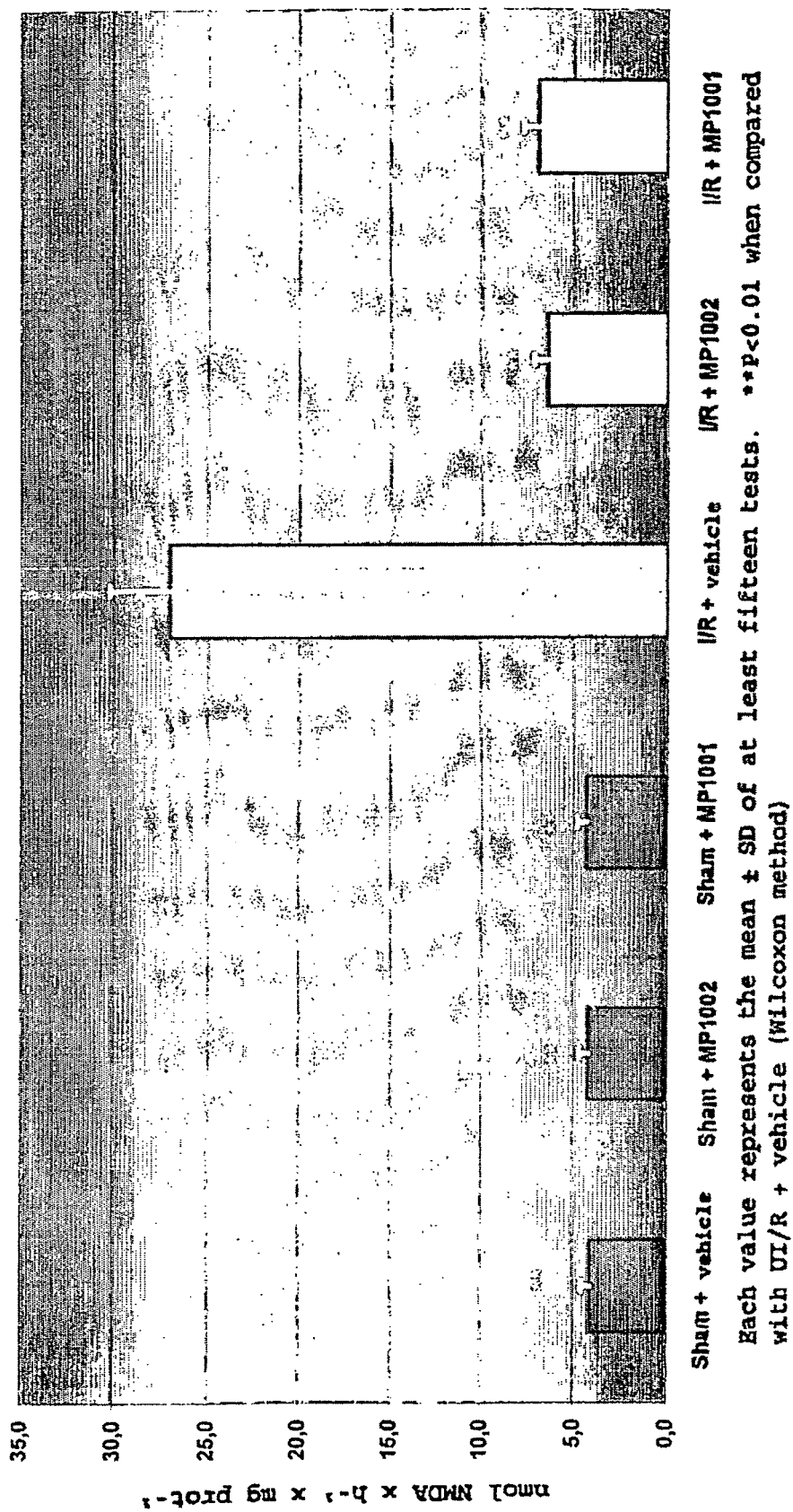

USE OF N-PIPERIDINE DERIVATIVES FOR THE TREATMENT OF NEURODEGENERATIVE PATHOLOGIES

It is known that oxygen-centred free radicals (ROS) and nitrogen-centred free radicals (RNS) are regularly generated during cell respiration and normal metabolism, performing important physiological functions such as, for example, that of second messengers in the induction of cell processes (Suzuki H. J. Free Rad. Biol. Med. 22, 269-285, 1977; Clement M. V. & Pervaiz S. Free Rad. Res. 30, 247-2525, 1999).

It is also known that a large and increasing number of pathological processes are associated with an increase in the generation of reactive radical species such as the superoxide anion ($O_2.^-$), the perhydroxyl radical ($HO_2.^-$), the hydroxyl radical (HO.), the oxygen singleton, ($^{1A}O_2$), hydrogen peroxide ($H_2O_2$), nitric oxide (NO.), nitrogen dioxide ($NO_2^-$), peroxynitrite and other (R.) radicals (alkyl-L., alkoxy-LO., peroxy-LOO. radicals, etc.).

The radicals which are produced in excess, saturating the antioxidizing machinery that is constituted both by enzymatic systems (superoxide dismutase, glutathione peroxidase, catalase, glutathione reductase) and by hydrophilic and lipophilic non-enzymatic systems (ubiquinone, ubiquinol, vitamin E, vitamin C, vitamin A, reduced glutathione, uric acid, carotenoids etc.) generate the much-proclaimed "oxidative stress state" (OSS) which is responsible for cell death and tissue damage: radical attack can result in a further increase in ROS, RNS and R., that is, in OSS, with consequent exacerbation of the initial oxidative damage (Diaz M. D. et al., New Engl. J. Med. 331, 408-416, 1997; Cerutti P. A., The Lancet 344, 862-863, 1994; Giacosa A. & Filiberti R. Eur. J. Cancer Prev. 5, 307-312, 1996; Bruce N. A. et al. Proc. Natl. Acad. Sci. (USA) 90, 1915-1922, 1993; Albens L. et al. J. Neural Transm. (Suppl.) 59, 133-154, 2000; Foley M. et al. J. Neurol. (Suppl. 2) 247, 1182-94, 2000; Huang Z. et al. Can J. Neurol. Sci. (Suppl. 1) 30, S10-18, 2003; He Y. et al. J. Neurochem. 86, 1338-1345, 2003; Gao H. M. et al. Trends Pharmacol. Sci. 24, 395-401, 2003; Sekhon B. et al. Brain Res. 971, 1-8, 2003; Nedelykovic Z. S. et al. Postgrad. Med. J. 79, 195-198, 2003; Arbiser J. L. Nat. Med. 9, 1103-1104, 2003; see also Medline® and Toxline®).

Furthermore, it is known to try to attenuate the cascade of events which leads to OSS by various therapeutic approaches each with inevitable problems which preclude or limit its use in man or in animals. Chelating agents which, for example, can catalyze undesired redox reactions in the cells, easily dissociate or lose activity as a result of bonds with multiple cell components (Ikeda Y. et al. Neurosurgery 24, 820-824, 1989; White B. C. & Krause G. S. Ann. Emerg. Med. 22, 970-979, 1993).

Apart from the limiting factor connected with enzyme saturation (5 turnover number) and with the individual dismutate reactive species ($O_2.^-$) in the more complex and dynamic world of OSS, the use of the enzyme superoxide dismutase poses problems of stability (even when included in liposomes) with a half-life variable between a few minutes and several hours according to type; it does not pass through the cell membranes and even less through the blood-brain barrier, and is immunogenic (although the recent use of recombinant human r-h-MnSOD forms seems encouraging) (Mikawa S. et al. J. Neurosurg. 85, 885-891, 1996; Kontos H. A. & Wei E. P. J. Neurosurg. 64, 803-807, 1986; Chan P. H. et al. Ann. Neur. 21, 540-547, 1987); it is not without significance that a recent randomized and multi-centre trial which provided for the use of glycol-conjugated superoxide dismutase (Pegorgotein®) in closed cranial traumas inevitably did not give the results that were hoped for (Young B. et al. JAMA 276, 538-543, 1996).

Some of the limitations connected with the use of the natural enzyme such as, for example, cell permeability—with particular reference to the blood-brain barrier—and administration, have been overcome with the use of organic compounds (for example M40401® or M40403®) with low molecular weight and with catalytic-dismutase activity, for example, towards the superoxide (SOD mimetics) (see U.S. Pat. Nos. 5,874,421, 5,637,578 and 5,696,109; International applications WO02/28390 and WO02/058686, Samilowski W. E. et al. Nat. Med. 9, 750-755, 2003), or even with the use of the isolated active portion of the enzyme (U.S. Pat. No. 6,117,454).

However, even these strategies can have only limited effectiveness since they reproduce the activity of the natural enzyme at molecular level; in fact they also act on a single radical species ($O_2.^-$) and are therefore completely inactive with respect to the others, ROS, RNS and R. which lead to OSS as a whole. At the moment, drugs which need to pass through the blood-brain membrane and which pass through it with difficulty or are unable to pass through it, have to be administered by direct infusion into the CNS or by controlled-release polymer implant, with problems which can easily be imagined (see, for example, U.S. Pat. No. 4,883, 666).

Further molecules which have been proposed are the so-called "spin-trapping scavenging agents" such as, for example, azulenyl nitrones, NXY-059 and, in particular, alpha-phenyl-tert-butyl nitrone (PBN) which has given satisfactory results in various pathologies (Rachnilewitz D. et al. Gut 35, 1181-1188, 1994; Krishna M. C. et al. J. Biol. Chem. 271, 26018-26025, 1996; Gilgun-Sherki Y. et al. Pharmacol. Rev. 54, 271-284, 2002). Once again, however, the action is limited to a few radical species since, although the action on the carbon-centred radicals (C·) leads to a relatively stable adduct, the bond with oxygen-centred radicals is completely unsatisfactory; suffice it to consider, for example that the half-life of the adduct between the undesirable hydroxyl radical (HO·) and PBN is just 40 seconds (Jansen F. G. et al. Free Rad. Biol. Med. 12, 169-173, 1992).

After fragmentation, these non-persistent nitroxides also give rise to further radical species which can propagate or initiate the auto-oxidation reaction. Moreover, PBN does not bind nitrogen-centred radicals (RNS) (Hensley K. et al. Int. Rev. Neurobiol. 40, 299-317, 1997). Spin traps which have greater stability in vitro (Tempo. Tempol), which can bind superoxide radicals ($O_2.^-$) and hydroxyl radicals (HO.), which can self-regenerate (that is, which do not have a suicide action like normal antioxidants), and which can simultaneously block Fenton's reaction, that is, which can terminate radical reactions, have been produced (Samuni et al. Biochemistry 30, 555-561, 1991; Samuni et al. J. Clin. Invest. 87, 1562-1530, 1991; Li H. et al. Free Rad. Biol. Med. 32 712-719, 2002; Krishna M. C. et al. J. Biol. Chem. 271, 26026-26031, 1996). However, the protective action of these molecules in vivo is limited both by their toxicity and by their half-life which is less than 3 minutes (Laight D. et al. Br. J. Pharmacol. 124, 238-244, 1988).

To overcome these difficulties, these spin-traps are in fact used in vivo in association with a polynitroxylated macromolecule (polynitroxyl human serum albumin, PNA) which reduces their toxicity, permits "recycling" and, if the dose used is kept low, prevents vasodilating effects (Kupposomi P. et al. Biochemistry 35 7051-7057, 1996; Kupposomi P. et al., Magn. Res. Med. 40, 806-811, 1998); naturally, given their considerable dimensions, these macromolecules function only in the extracellular spaces.

Pharmaceutical compositions comprising cyclic hydroxylamines derived from N-piperidine for the treatment of diseases connected with an excess production of free radicals have recently been described in U.S. Pat. No. 5,981,548.

SUMMARY OF THE INVENTION

A first aspect of the present invention is based on the recognition of the fact that the cyclic hydroxylamines derived from N-piperidine which are described in the above-mentioned U.S. Pat. No. 5,981,548 can pass through the blood-brain barrier and can therefore be used in the therapeutic treatment and prophylaxis of neurodegenerative diseases.

Within the scope of the invention, further compounds have been identified which are derived from N-piperidine and have pharmaceutical activity in the treatment of various pathologies indicated below, and for which no use in the pharmaceutical field has been proposed up to now.

With reference to these further compounds, the present invention provides for novel uses in therapy and prophylaxis which result from the identification of unexpected properties thereof such as, in particular, a high capacity to react with the various types of free radicals, terminating the radical reactions, the ability to pass easily through the double lipoprotein layer of the cell membranes (with particular reference to the blood-brain barrier), a high capacity for distribution within the tissues, thus enabling a high concentration of the active substance to be obtained in the region of the body in which antioxidant protection is required, and the ability to self-regenerate (self-replenishing antioxidants) and to prevent Fenton's reaction by the oxidation of metal ions.

A further object of the present invention is preferably that of providing for novel therapeutic uses with respect to a class of compounds which, in addition to all of the advantages mentioned above, are non-toxic, non-immunogenic, stable and easy to prepare in large quantities at low cost.

BRIEF DESCRIPTION OF THE DRAWINGS

The following is a brief description of the drawings, in which:

FIG. 1 is a graph showing the antioxidants MP 1002 and MP 1001 on the extent of myocardial infarction after occlusion and reperfusion of the left anterior descending coronary artery in rat; and FIG. 2 is a graph showing the effects of MP 1002 and MP 1001 on the development of lipid peroxidation in myocardial ischemia and reperfusion in rat.

DETAILED DESCRIPTION OF THE INVENTION

The novel therapeutic uses and the pharmaceutical compositions of the invention are defined in the appended claims.

In particular, the novel uses in the pharmaceutical field, which are described in greater detail below, relate to a class of compounds of formula (I):

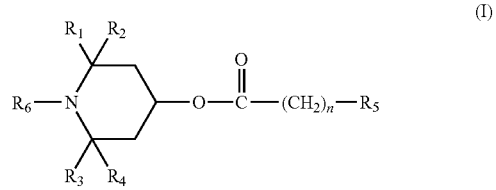

in which $R_6$ is oxyl, hydrogen or hydroxyl, $R_1$, $R_2$, $R_3$ and $R_4$ are selected independently of one another from:
  hydrogen
  alkyl with from 1 to 12 carbon atoms, preferably from 1 to 6 carbon atoms and more preferably from 1 to 3 carbon atoms,
  alkenyl with from 2 to 12 carbon atoms, preferably from 2 to 6 carbon atoms and more preferably from 2 to 3 carbon atoms,
  alkynyl with from 2 to 12 carbon atoms, preferably from 2 to 6 carbon atoms and more preferably from 2 to 3 carbon atoms, or
  $R_1$ and $R_2$ together form a tetramethylene or pentamethylene group;
  $R_5$ is hydrogen,
  alkyl with from 1 to 12 carbon atoms, preferably from 1 to 6 carbon atoms and more preferably from 1 to 3 carbon atoms,
  cycloalkyl with from 3 to 8 carbon atoms,
  alkenyl with from 2 to 12 carbon atoms, preferably from 2 to 6 carbon atoms and more preferably from 2 to 3 carbon atoms,
  alkynyl with from 2 to 12 carbon atoms, preferably from 2 to 6 carbon atoms and more preferably from 2 to 3 carbon atoms, or

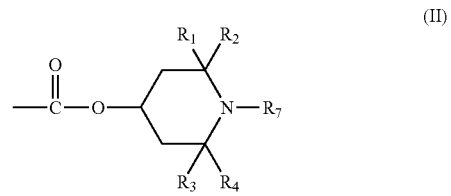

in which
  $R_1$, $R_2$, $R_3$ and $R_4$ are as defined above, n is a whole number from 1 to 30, more preferably from 2 to 14 and even more preferably from 6 to 10,
  $R_7$ is hydrogen, oxyl, or hydroxyl.

A group of compounds which are preferred and are illustrative of the present invention are compounds of formula:

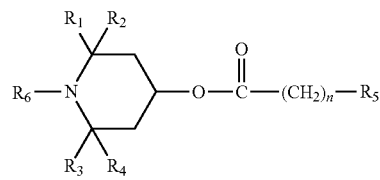

in which
  $R_1$, $R_2$, $R_3$ and $R_4$ are alkyl having from 1 to 3 carbon atoms,
  $R_5$ is

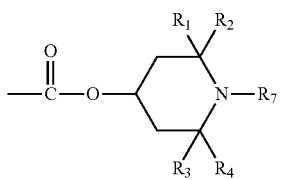

in which
R$_1$, R$_2$, R$_3$ and R$_4$ are alkyl having from 1 to 3 carbon atoms,
n is a whole number from 1 to 10 and at least one of R$_6$ and R$_7$ is oxyl and the other of R$_6$ and R$_7$ is oxyl or hydroxyl; in particular, the use of a compound of formula:

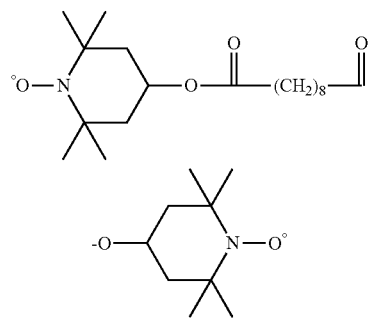

known as: bis(1-oxyl-2,2,6,6-tetramethyl-4-piperidinyl)decandioate is particularly preferred.

The term "alkyl with from 1 to 12 carbon atoms" denotes a substituent group derived from a saturated hydrocarbon by removal of a single hydrogen atom. The term includes methyl, ethyl, n-propyl, n-butyl, sec-butyl, iso-butyl, tert-butyl and the various isomeric forms of pentyl, hexyl, heptyl, octyl, nonyl, decyl, undecyl and dodecyl.

The terms "alkenyl having from 2 to 12 carbon atoms" and "alkenyl with from 2 to 12 carbon atoms" indicate substituent groups derived, respectively, from alkene and alkyne hydrocarbons by removal of a single hydrogen atom. These terms include ethenyl, ethynyl, propenyl, propynyl and similar branched and non-branched unsaturated hydrocarbon groups having up to 12 carbon atoms.

The term "cycloalkyl having from 3 to 8 carbon atoms" indicates saturated carbocyclic rings such as cyclopropyl, cyclobutyl, cyclopentenyl, cyclohexyl, as well as carbocyclic rings substituted with alkyl which contain up to 8 carbon atoms such as, for example, methyl-, dimethyl- and ethylcyclohexyl.

The N-oxyl and N-hydroxyl derivative compounds can be prepared by processes described in U.S. Pat. Nos. 4,691,015 and 5,981,548, starting with the N—H derivatives.

In particular, the N-oxyl derivatives are obtained from the corresponding N—H derivative by reaction with m-chloroperbenzoic acid. The N-oxyl derivative can be converted into the corresponding N-hydroxy derivative by catalytic hydrogenation, for example, with the use of PtO$_2$ as catalyst.

As indicated above, a subject of the invention is the use of the above-mentioned compounds for the preparation of medicaments, pharmaceutical or veterinary compositions for the treatment (inhibition, prevention, prophylaxis and therapy) of neurodegenerative syndromes and pathologies such as Parkinson's disease, Alzheimer's disease, encephalic lesions due to ictus, traumatic brain lesions, neuropathy due to HIV, Down's syndrome, diabetic polyneuropathy, muscular dystrophy, multiple sclerosis, Huntington's disease, prion disease, late dyskinesia, tauopathy, demyelinating pathologies and Lou Gherig's syndrome.

The invention also relates to the use of the compounds mentioned for the preparation of pharmaceutical or veterinary compositions and of medicaments for the therapeutic treatment, prevention, and/or prophylaxis of mortal conditions such as cardiac/renal/pulmonary/hepatic/intestinal ischaemia-reperfusion, hypertension, diabetes, cancer and also of shock, cystic fibrosis, virus infections, toxicity due to drugs and radiation (for example, radiotherapy or radiation protection more generally) inflammation, atherosclerosis, aging, rheumatoid arthritis, epilepsy, hypercholesterolaemia, hyperlipidaemia, as well as in the treatment of pain and sepsis, and pathologies associated with an excess production of free radicals.

For use in the pharmaceutical or veterinary field, the compounds according to the present invention are administered to the patient at dose levels within the range of from 0.01 to 1 g/kg of body weight, preferably from 0.1 to 200 mg/kg and more preferably within a range of between 0.5 and 20 mg/kg of body weight, in one or more daily administrations.

The specific dosages used, however, may vary in dependence on the needs of the patient or of the animal, on the severity of the pathologies to be treated (on age, sex, diet, method of administration, and on pharmacological considerations such as the activity of the compound to be used, the efficacy and the pharmacokinetic and toxicological profile of the preselected compound and of any combination with other drugs, etc.). The determination of the optimal dose is amongst the possible selections that are open to a person skilled in the art.

Pharmaceutically acceptable vehicles in both solid and liquid form may be used for the preparation of pharmaceutical or veterinary compositions comprising at least one of the compounds according to the present invention.

The methods of administration comprise, in addition to oral and parenteral administration, administration by inhalatory and dermatological (topical) routes.

The solid preparations will include, for example, powders, tablets, granules, capsules, cachets and suppositories.

A solid vehicle may be constituted by one or more substances which may also act as diluents, flavourings, solubilizers, lubricants, suspension agents, binders or disaggregants for tablets; encapsulated material may also be used.

In the powders, the vehicle is constituted by a finely divided solid which is mixed with at least one active compound. In tablets, the active ingredient is mixed with the vehicle having the necessary binding properties in suitable proportions and is compacted in the desired shape and size. The powders and tablets preferably contain between 7 and 70% by weight of the active ingredient.

Suitable vehicles are represented principally by magnesium carbonate, magnesium stearate, talc, lactose, sugar, pectin, dextrin, maize starch, methyl cellulose, sodium carboxymethyl cellulose, waxes with low melting points, coconut butter and the like.

Tablets, powders, cachets and capsules may be used as suitable forms of dosage for oral administration.

Preparations in liquid form include solutions suitable for parenteral administration (subcutaneous, intravenous, intramuscular, intrasternal injections or infusion techniques) or for oral administration, that is, suspensions and emulsions suitable for oral administration. Both sterile aqueous solutions of the active ingredient and sterile solutions of the active ingredient in solvents comprising water, ethanol, or propylene glycol may be mentioned as examples of liquid preparations suitable for parenteral administration.

Sterile solutions may be prepared by dissolving the active ingredient in the desired solvent system and then passing the resulting solution through a membrane filter in order to sterilize it or, alternatively, by dissolving the sterile compound in a previously sterilized solvent, in sterile conditions.

Aqueous solutions for oral administration may be prepared by dissolving the active ingredient in water and adding suitable colouring, flavouring, stabilizing, and agglomerating agents in the desired quantity.

Aqueous suspensions for oral use may be prepared by dispersing the finely divided active ingredient in water together with viscous material such as natural or synthetic cellulose and other suspension agents known in the art for pharmaceutical or veterinary formulations.

Preferably, the pharmaceutical or veterinary preparation is in the form of single-dose units preferably containing from 1 to 300 mg. In this form, the preparation is divided into unitary doses containing suitable quantities of the active ingredient. The single-dose unit may be constituted by a packaged preparation containing tablets, capsules, or powders in phials or ampoules.

The pharmaceutical compositions of the invention are preferably for use in man. However, since they are usable for man, they may also be useable in the veterinary field for pets, exotic animals and farm animals, including mammals, birds, rodents, etc., more preferably, animals such as dogs and cats, as well as cattle, sheep and pigs.

The following examples may enable a person skilled in the art to implement the invention. They will therefore be illustrative of the invention and are included solely as examples and not as a limitation. The use of the invention both in a model of Parkinson's disease, as an example of a neurodegenerative disorder, and in a model of myocardial ischaemia-reperfusion, as an example of a life-threatening disease, is therefore described.

EXAMPLE 1

Although Parkinson's syndrome (PS) was described for the first time in 1817 by James Parkinson as a "shaking palsy" of unknown origin (there is, however, evidence of parkinsonian syndromes dating back even thousands of years), its aetiology is still quite obscure.

In addition to age, there is lively scientific debate at international level on the role of genetic and environmental factors in the origin of PS (Huang Z et al. Can. J. Neur. Sci. 30 Suppl. 1, 510-518, 2003; Daner W. et al. Proc. Natl. Acad. Scie. (USA) 99, 14524-14529, 2002; Vaughan J. R. et al Am. Hum. Gen. 65, 111-126, 2001; Thiruchelvam M. et al. Neurotoxicology 23, 621-633, 2002; Scott W. K. et al. JAMA 286, 2239-2244, 2001; Warner T. T. & Schapira A. H. Am. Neurol. Suppl. 3, 516-523, 2003). A considerable impulse was given to research in the environmental field in the middle of the early nineteen-eighties by the discovery that specific neurotoxins such as n-methyl-4-phenyl-1,2,3,6-tetrahydropyridine (MTPT) can cause parkinsonism in man and in animals; since then, many pesticides have been found to reproduce PS in animal models (Betarbert R. et al. Nat. Neurosci. 3, 1301-1306, 2000; Kirbi M. L. et al, Toxicol. Sci. 61, 100-106, 2001; Yumino K. et al. J. Biochem. (Tokyo) 131, 565-570, 2002; Gao et al. J. Neurosci. 23, 6181-6187, 2003). It is not without significance that case-control meta-analysis of the studies available suggests the existence of an association between exposure to pesticides and PS (Priyadarshi A. et al. Neurotoxicology 21, 435-440, 2000; Priyadarshi A. et al. Environ. Res. 86, 123-127, 2001).

Much experimental evidence demonstrates that the herbicide Paraquat (which has a chemical structure similar to MPTP) is involved in the pathogenesis of PS; both microinfusion of Paraquat into the Substantia Nigra of the animal and systemic or intraperitoneal treatment lead to selective degeneration of dopaminergic neurons accompanied by behavioural and neuropathological signs of severe non-selective neurotoxicity (Brooks A. I. et al. Brain Res. 823, 1-10, 1999; Thiruchelvam M. et al. Neurotoxicology 23, 621-633, 2002; McCornack A. L. et al. Neurobiol Dis. 10, 119-127, 2002) attributed to an excess of OSS-reactive free radicals (Jannone N. et al. Neuropharmacology 30, 893-898, 1991; Klivenyi G. et al Neurobiol. Dis. 5, 253-258, 1998; Foley M. et al. J. Neurol. 247 Suppl. 2, 1182-94, 2000).

The Paraquat/rat/PS experimental model was therefore selected as the most indicative for checking the efficacy of chemical compounds according to the present invention; of these, two anti-oxidants designated MP1002 and MP1001 were used in the tests:

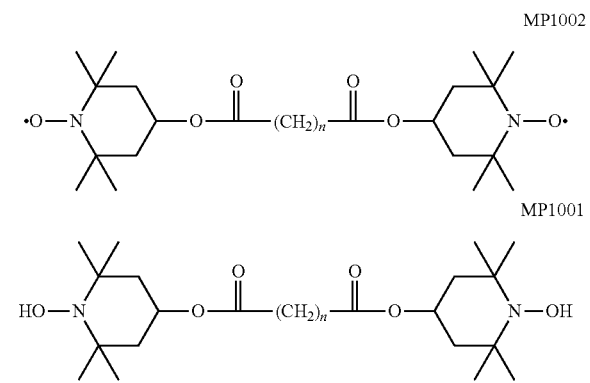

Male Sprague Dawley rats (210-220 g weight) were kept on a standard laboratory diet supplemented with "Nossan Pellets" (both the animals and the pellets are available from Nossan Company, Milan, Italy) and were housed for three weeks (relative humidity 50%±10%, temperature 22° C.±1 and in a light/darkness cycle of 12 hours/12 hours, with first light at 7.30 a.m.) prior to the tests; food and water were available ad libitum.

Prior to treatment, the rats were anaesthetized by intraperitoneal injection of 380 mg/kg weight of chloral hydrate; a stainless steel guide cannula (size 25) was implanted unilaterally in the Substantia Nigra with stereotaxic guiding and was secured to the cranium with dental acrylic material.

The animals (20 per test group) were allowed a recovery period of seven days prior to treatment; during this period no change in motor activity or posture was observed. Microinfusions were performed by means of a 10 μl Hamilton syringe connected to an injection cannula by means of a Teflon tube. The compounds or the vehicle (0.8% NaCl) were injected at a total volume of 1 μl/minute.

Microinfusion of 50 μg of Paraquat into the Substantia Nigra (n=20 rats) led to an increase in motor activity with the animals performing jumps and moving in circles in a contralateral direction relative to the injection position, about 24 minutes later; all of the animals were dead 24±2.5 hours after infusion. A further twenty animals were infused with Paraquat and twenty with Paraquat plus vehicle; about ten of the animals for each group survived 20 hours after treatment and were used to determine the development of lipid peroxidation in the Substantia Nigra.

When the Paraquat (50 μg) was microinfused into the Substantia Nigra simultaneously with 1 μg of MP1002 or MP1001, all of the animals survived for a further 24 hours and no signs of alterations were observed during continuous monitoring (see Table 1). Similar results were obtained after intraperitoneal administration of the anti-oxidants, thus demonstrating the extraordinary capacity of MP1002 or MP1001 to cross the blood-brain barrier (BBB), which is one of the most limiting factors of conventional antioxidants (together with their selectivity in relation to a specific type of radical) for therapeutic purposes in neurodegenerative pathologies.

In particular, none of the rats died when: (1) they were pre-treated intraperitoneally with 120 mg/kg by weight of MP1002 or MP1001 5 minutes prior to microinfusion of 50 μg of Paraquat; (2) they were simultaneously treated by intraperitoneal injection of 120 mg/kg by weight of MP1002 or MP1001 and infused with 50 μg of Paraquat; and (3) they were microinfused with 50 μg of Paraquat followed by intraperitoneal injection of 120 mg/kg by weight of MP1002 and MP1001 5 minutes later (see Table 1).

Lipid peroxidation in the Substantia Nigra was determined by quantification of the release of malondialdehyde (MDA) which was used as a biomarker, by means of the reagent thiobarbituric acid-TCA-HCl, as described by Buege J. A. & Aust S. D. Meth. Enzymol. 52, 302-310, 1978. Table 1 shows clearly the increase in lipid peroxidation in the Substantia Nigra in an additional group of animals (about ten) which survived 20 hours after infusion with 50 μg of Paraquat or Paraquat and saline solution. Treatment with MP1002 or MP1001 in the various situations (before, with, or after infusion with Paraquat) markedly and significantly ($p<0.01$) reduced lipid peroxidation in the Substantia Nigra, clearly indicating the high antioxidant potency of those compounds.

In these tests, both the intracerebral administration and the peripheral administration of MP1002 or MP1001, two types of antioxidant described herein, protected completely against the behavioural and neuropathological effects induced by Paraquat in rats. These results show the capacity of the compounds according to the invention to cross the brain-blood barrier easily thus protecting the dopaminergic neurons of the Substantia Nigra against degenerative damage (for example OSS) produced by herbicides such as Paraquat. This represents a useful approach for the treatment of various neurodegenerative pathologies, including Parkinson's disease.

EXAMPLE 2

The in vivo model of myocardial lesion due to ischaemia and reperfusion was selected as the most suitable for checking the efficacy of the compounds MP1002 and MP1001 according to the invention.

Male Sprague Dawley rats (220-230 g) were kept on a standard laboratory diet supplemented with "Nossan Pellets" (Nossan Company, Milan, Italy) and were housed for three weeks prior to the tests (relative humidity 50%±10, temperature 22° C.±1 and light/darkness cycle of 12/12 hours with first light at 7.30 a.m.); food and water were available ad libitum.

The rats (twenty per group) were anaesthetized by intraperitoneal injection of chloral hydrate (380 mg/kg) and were then tracheotomized, intubated and ventilated with ambient air by a suitable ventilator; body temperature was kept at 38° C.±1 and the right carotid artery was cannulated and connected to a pressure transducer to monitor the mean arterial blood pressure (MAP).

The right jugular vein was cannulated for the administration of the compounds, a lateral thoracotomy was performed, the heart was suspended in a temporary pericardial cradle, and a loop occluder was arranged around the left descending coronary artery (LAD); the animals were allowed to stabilize for 40 minutes prior to the LAD ligature.

The coronary artery was occluded by tightening the occluder, a procedure which is correlated with the electrocardiographic and haemodynamic changes (drop in MAP) which are typical of myocardial ischaemia. After 25 minutes of myocardial ischaemia, the occluder was reopened, permitting reperfusion for 2 hours. The heart rate (HR) and MAP were monitored continuously.

After reperfusion for 2 hours, the coronary artery was occluded again and the dye Evans blue was injected (4.5 ml at 2% p/v) into the left ventricle by means of the cannula in the right carotid artery in order to discriminate between perfused and non-perfused sections (AAR) of the heart; the Evans blue solution dyed the perfused myocardium whereas the occluded vascular bed remained undyed.

The rats were then killed by an overdose of anaesthetic, the hearts were removed and were cut into slices (3-4 mm), the right ventricular wall and the area at risk (pink) was removed and was separated from the non-ischaemic area (blue). The area at risk was cut into small pieces and incubated with tetrazolium p-nitro blue (NBT, 0.48 mg/ml) for 20 minutes at 37° C.; in the presence of intact dehydrogenase enzymes (live myocardium) the NBT formed a dark blue formazane whereas the area of necrosis without dehydrogenase activity was not coloured. The pieces were separated according to their coloration and were weighed to determine the size of the infarct as a percentage of the weight of AAR.

The following test groups were considered: a) LAD occlusion (25 minutes) and reperfusion (2 hours) plus administration of the vehicle (saline solution, 3 ml/kg-v-bolus plus 1.8 ml/kg/h) starting 5 minutes after reperfusion and maintained during the reperfusion period; b) LAD occlusion and reperfusion plus administration of MP1002 or MP1001 (10 mg/kg injection in bolus) 5 minutes prior to reperfusion, followed by infusion of 2 mg/kg/h during the reperfusion period; c) sham operation (no LAD occlusion) and infusion of the vehicle; d) sham operation and infusion of MP1002 or MP1001 as described above.

The malondialdehyde (MDA) in the heart tissue as final peroxidation product of the cell membrane lipids was also determined as described above.

Table 2 gives the various MPA and HR values measured during the course of the tests. The base haemodynamic results were similar in the various groups considered.

In the animals receiving sham operations (no LAD occlusion) the infusion of the vehicle or vehicle with MP1002 or MP1001 had no substantial haemodynamic effects.

In the animals which were subjected to coronary occlusion and reperfusion, the mean MAP values were reduced slightly during the test period but there were no changes in HR. Moreover, the mean MAP and HR values of the rats which were subjected to I/R (ischaemia/reperfusion) treatment and treated with MP1002 or MP1001 were not significantly different from the I/R group treated with the vehicle alone.

The infusion of MP1002 or MP1001 brought about a significant reduction ($p<0.01$) in the size of the infarct (80% and 78%, respectively) when compared with the control (FIG. 1). The sham operation did not result in a significant degree of infarct. Whereas the I/R treatment led to a marked and significant increase ($p<0.01$) in lipid peroxidation in comparison with the rats that were subjected to sham operations (plus vehicle or antioxidant), treatment with MP1002 or MP1001 significantly ($p<0.01$) reduced the development of peroxidation to levels similar to those of the animals that were subjected to sham operations (FIG. 2), thus providing evidence of the high antioxidant power of these compounds.

These tests show that MP1002 and MP1001 can drastically reduce the size of myocardial infarcts after occlusion and reperfusion of the myocardium. These results demonstrate the capacity of the compounds of the invention to exert a good protective effect against myocardial lesions induced by ischaemia-reperfusion.

This suggests that the compounds of the invention offer a novel therapeutic approach for the treatment of life-threatening diseases including ischaemic heart diseases.

damage in an animal, comprising administering an effective amount of a compound having the formula:

TABLE 1

EFFECTS OF EITHER BIS(1-OXYL-2,2,6,6-TETRAMETHYL-4-PIPERIDINYL)DECANDIOATE (MP1002) OR BIS(1-HYDROXYL-2,2,6,6-TETRAMETHYL-4-PIPERIDINYL)DECANDIOATE (MP1001) ON THE LATENCY, DURATION OF SEIZURES, MORTALITY AND LIPID PEROXIDATION DEVELOPMENT IN RATS RECEIVING PARAQUAT INTO SUBSTANTIA NIGRA

| Treatment | Latency (min) | Duration (min) | Mortality (%) | Lipid Peroxidation (nmol MDA × $h^{-1}$ × mg $prot^{-1}$) |
|---|---|---|---|---|
| Control | 0 | 0 | 0 | 3.8 ± 0.76 |
| Paraquat* | 25 ± 4 | 270 ± 15 | 100 (20/20) | 14.6 ± 1.34** |
| Paraquat + vehicle* | 25 ± 6 | 266 ± 17 | 100 (20/20) | 13.5 ± 1.10** |
| Paraquat + MP1002[a] | No seizures and epileptic discharges | No seizures and epileptic discharges | 0 | 4.3 ± 0.63** |
| Paraquat + MP1001[a] | No seizures and epileptic discharges | No seizures and epileptic discharges | 0 | 5.4 ± 0.84** |
| Paraquat + MP1002[b] | No seizures and epileptic discharges | No seizures and epileptic discharges | 0 | 5.2 ± 0.75** |
| Paraquat + MP1001[b] | No seizures and epileptic discharges | No seizures and epileptic discharges | 0 | 4.7 ± 0.49** |
| Paraquat + MP1002[c] | No seizures and epileptic discharges | No seizures and epileptic discharges | 0 | 4.9 ± 0.86** |
| Paraquat + MP1001[c] | No seizures and epileptic discharges | No seizures and epileptic discharges | 0 | 5.1 ± 0.94** |
| Paraquat + MP1002[d] | No seizures and epileptic discharges | No seizures and epileptic discharges | 0 | 4.1 ± 0.39** |
| Paraquat + MP1001[d] | No seizures and epileptic discharges | No seizures and epileptic discharges | 0 | 4.8 ± 0.57** |

Each value represents the mean ± SD of twenty different experiments performed on twenty different rats;
[a] animals received by simultaneous microinfusion into Substantia Nigra paraquat (50 μg) either with 1 μg MP1002 or MP1001;
[b] animals pretreated intraperitoneally with 120 mg/kg b.w. of either MP1002 or MP1001 and, after 5 minutes, receiving paraquat (50 μg) by microinfusion;
[c] animals received simultaneously 50 μg paraquat by microinfusion with 120 mg/kg b.w. of either MP1002 or MP1001 by intraperitoneal injection;
[d] animals received 50 μg paraquat by microinfusion and, 5 minutes later, 100 mg/kg b.w. of either MP1002 or MP1001 by intraperitoneal injection.
In the Table are also reported changes of lipid peroxidation into Substantia Nigra as malondialdehyde (MDA) levels after 24 or 20(*) hours from treatment. See text for details and experimental procedures.
**$p<0.01$ paraquat or paraquat + vehicle vs control and paraquat + vehicle vs MP1002 or MP1001-treated groups (Wilcoxon's rank method).

TABLE 2

EFFECTS OF THE ANTIOXIDANTS MP1002 AND MP1001 ON MEAN ARTERIAL BLOOD PRESSURE (MAP) AND HEART RATE (HR) CHANGES IN MYOCARDIAL ISCHAEMIA AND REPERFUSION (I/R) IN THE RAT

| Group | | Baseline | Occlusion (min) | | Reperfusion (min) | |
|---|---|---|---|---|---|---|
| | | | 15 | 25 | 15 | 25 |
| Sham + vehicle | MAP | 128 ± 12 | 126 ± 14 | 118 ± 10 | 112 ± 9 | 105 ± 12 |
| | HR | 425 ± 25 | 429 ± 26 | 426 ± 21 | 431 ± 23 | 429 ± 22 |
| Sham + MP1002 | MAP | 125 ± 15 | 123 ± 16 | 120 ± 11 | 110 ± 12 | 105 ± 9 |
| | HR | 421 ± 26 | 420 ± 33 | 422 ± 25 | 428 ± 26 | 426 ± 32 |
| Sham + MP1001 | MAP | 127 ± 16 | 125 ± 13 | 121 ± 11 | 112 ± 8 | 107 ± 16 |
| | HR | 422 ± 33 | 422 ± 26 | 424 ± 48 | 427 ± 27 | 427 ± 23 |
| I/R + vehicle | MAP | 128 ± 10 | 121 ± 12 | 113 ± 10 | 101 ± 12 | 96 ± 9 |
| | HR | 445 ± 34 | 440 ± 31 | 436 ± 27 | 434 ± 28 | 436 ± 26 |
| I/R + MP1002 | MAP | 127 ± 14 | 121 ± 14 | 114 ± 10 | 102 ± 11 | 97 ± 9 |
| | HR | 438 ± 30 | 437 ± 32 | 431 ± 24 | 427 ± 29 | 429 ± 25 |
| I/R + MP1001 | MAP | 125 ± 9 | 118 ± 12 | 111 ± 13 | 100 ± 10 | 95 ± 8 |
| | HR | 435 ± 25 | 438 ± 31 | 430 ± 28 | 425 ± 28 | 427 ± 26 |

Each value represents the mean ± SD of at least fifteen different experiments. Animals received MP1002, MP1001 or an equal volume of vehicle. See text for details and experimental procedures.

The invention claimed is:

1. A method of inhibiting or therapy of Alzheimer's disease, Parkinson's disease, stroke and ischemia/reperfusion injury, diabetes mellitus, hypertension, sepsis and radiation

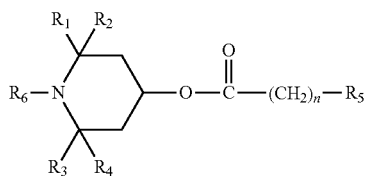

(I)

in which:

R$_6$ is oxyl, hydrogen or hydroxyl, R$_1$, R$_2$, R$_3$ and R$_4$ are selected independently of one another from:
hydrogen
alkyl having from 1 to 6 carbon atoms,
R$_5$ is

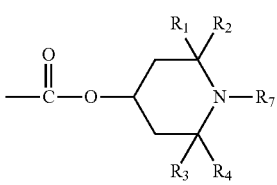

(II)

in which:

R$_1$, R$_2$, R$_3$ and R$_4$ are as defined above,

R$_7$ is the same as or different from R$_6$ and is selected from hydrogen, oxyl or hydroxyl, and n is a whole number from 6 to 10, wherein said compound is administered by oral, subcutaneous, intravenous, intramuscular, or intrasternal administration.

2. The method according to claim 1 in which R$_1$, R$_2$, R$_3$ and R$_4$ are, independently of one another, an alkyl having from 1 to 3 carbon atoms and R$_5$ is:

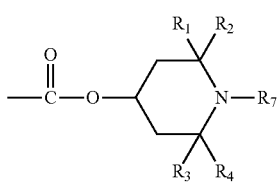

in which R$_1$, R$_2$, R$_3$ and R$_4$ are, independently of one another, an alkyl having from 1 to 3 carbon atoms, R$_7$ is oxyl, hydrogen or hydroxyl, and n is a whole number from 6 to 10.

3. The method according to claim 1 in which the compound is of formula:

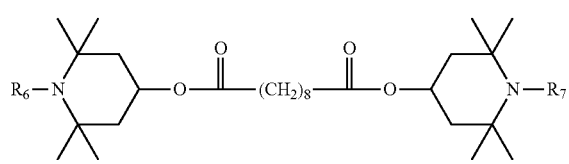

(III)

in which R$_6$ and R$_7$ are identical or different and are selected from oxyl, and hydroxyl.

4. The method according to claim 1 in which the disease is a neurodegenerative disease is selected from Parkinson's disease, Alzheimer's disease, brain lesion due to ischaemia-reperfusion.

5. The method of claim 1 for the treatment of pathologies selected from lesions due to ischaemia-reperfusion hypertension, diabetes, toxicity due to radiation in radiotherapy or radiation protection or sepsis.

6. The method according to claim 1 wherein the compound is in the form of a pharmaceutical or veterinary composition or medicament suitable for oral, inhalatory or topical administration.

7. The method according to claim 6 comprising administering the pharmaceutical or veterinary composition or medicament in a dosage form suitable for administration of the compound in quantities of from 0.01 to 200 mg/kg of body weight.

8. A method of inhibiting or therapy of the symptoms of Parkinson's disease or the symptoms of ischemia/reperfusion injury comprising administering a compound to a patient in an amount effective to inhibit or for the therapy of the symptoms of Parkinson's disease or the symptoms of ischemia/reperfusion injury and where the compound of formula (I) is selected from the group consisting of bis(1-oxyl-2,2,6,6-tetramethyl-4-piperidinyl)decandioate and bis(1-hydroxy-2,2,6,6-tetramethyl-4-piperidinyl)decandioate.

9. The method of claim 7 wherein the dosage is 0.5 to 20 mg/kg of body weight.

10. A method of inhibiting the symptoms of Parkinson's disease or ischemia/reperfusion injury in an animal, comprising administering an effective amount of a compound having the formula:

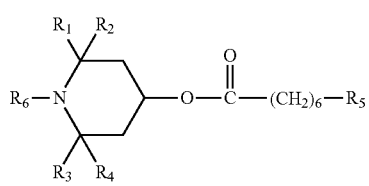

(I)

in which:

R$_6$ is oxyl, hydrogen or hydroxyl, R$_1$, R$_2$, R$_3$ and R$_4$ are selected independently of one another from:
hydrogen
alkyl having from 1 to 6 carbon atoms,
R$_5$ is

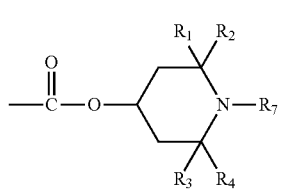

(II)

in which:

R$_1$, R$_2$, R$_3$ and R$_4$ are as defined above,

R$_7$ is the same as or different from R$_6$ and is selected from hydrogen, oxyl or hydroxyl, and n is a whole number from 6 to 10.

11. The method of claim 10, wherein said compound is administered by oral, subcutaneous, intravenous, intramuscular, or intrasternal administration.

* * * * *